United States Patent [19]
Kellner et al.

[11] Patent Number: 4,873,381
[45] Date of Patent: Oct. 10, 1989

[54] HYDRODEHALOGENATION OF CF$_3$CHCLF IN THE PRESENCE OF SUPPORTED PD

[75] Inventors: Carl S. Kellner; V. N. Mallikarjuna Rao, both of Wilmington, Del.

[73] Assignee: E. I. Du Pont de Nemours and Company, Wilmington, Del.

[21] Appl. No.: 199,811

[22] Filed: May 20, 1988

[51] Int. Cl.$^4$ .................... C07C 17/24; C07C 19/02
[52] U.S. Cl. .................................................. 570/176
[58] Field of Search ......................................... 570/176

[56] References Cited

U.S. PATENT DOCUMENTS

| | | | |
|---|---|---|---|
| 2,942,036 | 6/1960 | Smith et al. | 570/176 |
| 3,439,052 | 4/1969 | Bjornson | 570/176 |
| 3,636,173 | 1/1972 | Gardner | 570/176 |

FOREIGN PATENT DOCUMENTS

| | | | |
|---|---|---|---|
| 3619079 | 12/1986 | Fed. Rep. of Germany | 570/176 |
| 1578933 | 11/1980 | United Kingdom | 570/176 |

OTHER PUBLICATIONS

Gervasutti et al., *Journal of Flourine Chemistry*, 19, 1–20 (1981–1982).
AFOSR Document No. TR-58-99, Astia No. AD 162 198.

*Primary Examiner*—J. E. Evans

[57] ABSTRACT

Process for the manufacture of 1,1,1,2-tetrafluoroethane by the vapor phase hydrodehalogenation of 1,1,1,2-tetrafluorochloroethane in the presence of a catalyst consisting essentially of palladium on an aluminum fluoride or fluorinated alumina support.

6 Claims, No Drawings

HYDRODEHALOGENATION OF CF₃CHCLF IN THE PRESENCE OF SUPPORTED PD

FIELD OF THE INVENTION

Process for the manufacture of 1,1,1,2-tetrafluoromonochloroethane by the vapor phase hydrodehalogenation of 1,1,1,2-tetrafluorochloroethane in the presence of a catalyst consisting essentially of palladium supported on aluminum fluoride or fluorinated alumina.

BACKGROUND OF THE INVENTION

A common method for preparing 1,1,1,2-tetrafluorochloroethane is contacting tetrachloroethylene with HF in the presence of a catalyst. While many variations on this method are useful, a preferred method is described in commonly assigned application No. 070826, filed July 7, 1987 which utilizes a gas-phase reaction of a tetrahaloethylene with HF in the presence of a selected metal salt on a high-fluorine-content alumina support, and minimizes the production of pentafluoroethane. The produced 1,1,1,2-tetrafluorochloroethane can then be hydrodehalognated to the desired 1,1,1,2-tetrafluoroethane.

GB 1,578,933 discloses and claims a process for the manufacture of tetrafluoroethanes having the formula $CHF_2CHF_2$ and $CF_2CH_2F$ characterized in that a haloethane having four or five fluorine atoms of formula $CF_2XCFYZ$ is reacted with hydrogen at an elevated temperature in the presence of a hydrogenation catalyst. In the formula X is fluorine or chlorine; and when X is fluorine, Y is chlorine or fluorine; and when Y is chlorine, Z is chlorine, fluorine or hydrogen; and when Y is fluorine, Z is hydrogen; and when X is chlorine, Y is fluorine and Z is either chlorine or hydrogen. Examples of hydrognation catalysts include nickel or metals of Group VIIIa of the Periodic Table or oxides of salts thereof.

Example 7 of the above patent discloses the hydrogenation of 1,1,1,2-tetrafluorochloroethane to produce 1,1,1,2-tetrafluoroethane using 5% palladium on charcoal as the catalyst. The selectivities to 1,1,1,2-tetrafluoroethane over a temperature range of 280° C. to 420° C. range from 95.8% to 97.3%.

C. Gervasutti et al., Journal of Fluorine Chemistry, 19, 1–20 (1981/82) disclose the preparation of 1,1,1,2-tetrafluoromonochloroethane from isomeric mixtures of dichlorotetrafluoroethanes through selective hydrogenolysis of $CF_3CCl_2F$ catalyzed by palladium/carbon.

The hydrodehalogenation or hydrogenolysis of 1,1,1,2-tetrafluoromonochloroethane by the above processes produces some $CF_3CH_3$, which results in the formation of HF in the effluent. This necessitates the removal of HF from the final product. It would be desirable to be able to hydrodehalogenate 1,1,1,2-tetrafluorochloroethane with essentially quantitative selectivity thus avoiding the need for HF separation and with maximum product yield.

This invention provides a process for preparing 1,1,1,2-tetrafluoroethane useful as a refrigerant via hydrodehalogenation of 1,1,1,2-tetrafluoromonochloroethane in the presence of a catalyst consisting essentially of palladium supported on aluminum fluoride or fluorinated alumina whose selectivity is essentially quantitative.

SUMMARY OF THE INVENTION

This invention provides for a process for the preparation of 1,1,1,2-tetrafluoroethane comprising contacting in the gaseous phase at a temperature of 200° C. to 350° C. 1,1,1,2-tetrafluoromonochloroethane with $H_2$ in the presence of a catalyst consisting essentially of palladium on an aluminum fluoride or fluorinated alumina support.

DETAILS OF THE INVENTION

The catalyst suitable for the process of this invention consists essentially of palladium on an aluminum fluoride or fluorinated alumina support. The catalyst of the instant invention can be prepared by impregnating aluminum fluoride with a solution of palladium compound. When the support is fluorinated alumina, the alumina can be fluorinated before or after the deposition of palladium. The concentration of palladium on the support can range from 0.1% to 10% by weight. The aluminum fluoride support can be prepared by fluorination of alumina at elevated temperatures. It is preferred that the fluorine content of the support be sufficient to provide a fluorine to aluminum ratio of at least 2.4. The aluminum fluoride or fluorinated alumina support utilized in the instant invention has the advantage of being regenerated by conventional means, which carbon-based supports do not have.

The reaction temperature can range from 200° C. to 350° C. A preferred range is 250° C. to 300° C.

The amount of hydrogen contained in the gas stream contacted with the gaseous 1,1,1,2-tetrafluoromonochloroethane should be at least 0.5 moles per mole of 1,1,1,2-tetrafluoromonochloroethane and, preferably from 0.5 to 3 moles for reasons of economics.

The 1,1,1,2-tetrafluoromonochloroethane utilized in the process of this invention can be prepared by any means well known in the art. A convenient source of 1,1,1,2-tetrafluoromonochloroethane is the effluent stream from the catalyzed gas phase reaction of tetrachloroethylene with HF.

The hydrodehalogenation of 1,1,1,2-tetrafluorochloroethane with hydrogen may be conducted in any suitable reactor, including fixed and fluidized bed reactors. The reaction vessel should be constructed from materials which are resistant to the corrosive effects of hydrogen halide such as "Hastelloy" and "Inconel".

Pressure is not critical. Atmospheric and superatmospheric pressures are the most convenient and are therefore preferred.

Unreacted 1,1,1,2-tetrafluoromonochloroethane may be recycled to the reactor for additional production of 1,1,1,2-tetrafluoroethane.

The present process has the advantage that the desirable 1,1,1,2-tetrafluoroethane can be obtained with essentially quantitative selectivity.

EXAMPLES

The examples below illustrate the practice of the invention.

EXAMPLE A

Preparation of the Support

The reactor (a 0.5 inch ID, 12 inch long "Inconel" pipe) was charged with 20 g. of alumina and placed into a sand bath. The bath was gradually heated to 400° C. while dry nitrogen gas at a flow rate of 50 ml/minute was passed through the reactor to remove traces of water. The temperature was lowered to 200° C., and an HF and nitrogen gas mixture (1:4 molar ratio) was passed through the reactor. The nitrogen flow was decreased with time until neat HF was being passed through the reactor. At this point, the temperature was gradually raised to 450° C. and maintained there for 300 minutes. It was then cooled under nitrogen to room temperature prior to use.

EXAMPLE B

Preparation of 5% Pd Supported Catalyst

Palladium acetate, 570 mg, was dissolved in 4.4 g. of $CH_2Cl_2$ and added to 5 g of the support as prepared in Example A. The solid was then dried and reduced insitu with hydrogen at 300° C. prior to the start of the reaction.

EXAMPLE C

Preparation of 2% Pd Supported Catalyst

This catalyst was prepared as described in Example B using 230 mg $Pd(OOCCH_3)_2$.

EXAMPLES 1-10

Procedure for Hydrodehalogenation

For Examples 1-10, the reactor, a ¼" "Inconel" tube, was charged with the amount of supported palladium (20×30 mesh) shown in Table 1. The reactor was maintained at the temperature shown in Table 1 by means of a fluidized sand bath and at the pressure shown in Table 1 using a back-pressure regulator. To the reactor was fed $CF_3CHClF$, as liquid which was vaporized prior to entering the reactor, and hydrogen at the rates shown in Table 1. The products leaving the reactor were analyzed by gas chromatography.

The analytical results shown in Table 1 illustrate the high selectivities in accordance with the invention.

TABLE 1

| Ex. | Cat. | Pres. (psig) | Temp. (°C.) | $H_2$ (ml/min) | $CF_3CHClF$ (ml/hr.) | $CF_3CHClF$ (conv.) | $CF_3CH_2F$ (sel.) |
|---|---|---|---|---|---|---|---|
| 1. | 0.87 g[a] | 180 | 225 | 6 | 1.0 | 16% | ~100% |
| 2. | 0.87 g[a] | 180 | 250 | 6 | 1.0 | 36% | 99% |
| 3. | 0.87 g[a] | 180 | 275 | 6 | 1.0 | 76% | 99% |
| 4. | 0.87 g[a] | 180 | 250 | 12 | 2.0 | 27% | 99% |
| 5. | 0.87 g[a] | 180 | 275 | 12 | 1.0 | 70% | 99% |
| 6. | 0.87 g[a] | 180 | 275 | 4 | 1.0 | 57% | 99% |
| 7. | 1.76 g[b] | 200 | 250 | 6 | 2.0 | 50% | 99% |
| 8. | 1.76 g[b] | 180 | 225 | 6 | 1.0 | 30% | 99% |
| 9. | 1.76 g[b] | 180 | 225 | 12 | 1.0 | 28% | 99% |
| 10. | 1.76 g[b] | 180 | 275 | 8 | 2.0 | 65% | 99% |

[a]5% Pd
[b]2% Pd

What is claimed is:

1. A process for the preparation of 1,1,1,2-tetrafluoroethane comprising contacting in the gaseous phase at a temperature of 200° C. to 350° C. 1,1,1,2-tetrafluoromonochloroethane with $H_2$ in the presence of a catalyst consisting essentially of palladium on an aluminum fluoride or fluorinated alumina support.

2. The process of claim 1 wherein the temperature is from 250° C. to 300° C.

3. The process of claim 1 wherein the concentration of the palladium on the support can range from 0.1% to 10% by weight.

4. The process of claim 1 wherein the support is prepared by fluorination of alumina at elevated temperatures.

5. The process of claim 1 wherein the fluorine content of the support corresponds to a fluorine to aluminum ratio of at least 2.4.

6. The process of claim 1 wherein the amount of $H_2$ is from 0.5 to 3 moles per mole of 1,1,1,2-tetrafluoromonochloroethane.

* * * * *